United States Patent [19]

Dailey

[11] 4,441,979

[45] Apr. 10, 1984

[54] NUTATING PROBE FOR GAS ANALYSIS

[75] Inventor: Leo L. Dailey, Philadelphia, Pa.

[73] Assignee: Fischer & Porter Company, Warminster, Pa.

[21] Appl. No.: 499,777

[22] Filed: May 31, 1983

[51] Int. Cl.³ .......................................... G01N 27/30
[52] U.S. Cl. ..................................... 204/402; 204/415
[58] Field of Search ................ 204/415, 1 P, 1 B, 402

[56] References Cited

U.S. PATENT DOCUMENTS

| | | | |
|---|---|---|---|
| 3,275,541 | 9/1966 | Strong | 204/415 X |
| 3,360,451 | 12/1967 | Stack | 204/415 |
| 3,413,199 | 11/1968 | Morrow | 204/1 T |
| 3,445,364 | 5/1969 | Strickler | 204/405 |
| 3,496,084 | 2/1970 | Stack | 204/415 X |
| 3,948,746 | 4/1976 | Poole | 204/415 X |
| 4,176,032 | 11/1979 | Stevenson | 204/415 |

Primary Examiner—G. L. Kaplan

Attorney, Agent, or Firm—Michael Ebert

[57] ABSTRACT

A probe immersible in process water or wastewater having oxygen, chlorine or another gas dissolved therein and adapted to continuously and accurately measure the concentration of the gas. The probe includes a noble metal measuring electrode, an oxidizable metal counter-electrode and an electrolyte which in combination with the electrodes defines an electrochemical cell whose output current depends on the amount of the gas passing into the cell through a diffusion membrane permeable to the gas being analyzed. In order to simulate the effect of rapid sample flow past the membrane and thereby maintain the analytical sensitivity of the instrument, the probe is vertically supported through a flexible coupling and includes an internal motor having an unbalanced rotor secured to its shaft. Rotation of the rotor causes the probe to nutate about its vertical axis to simulate the effect of a rapid sample flow.

9 Claims, 3 Drawing Figures

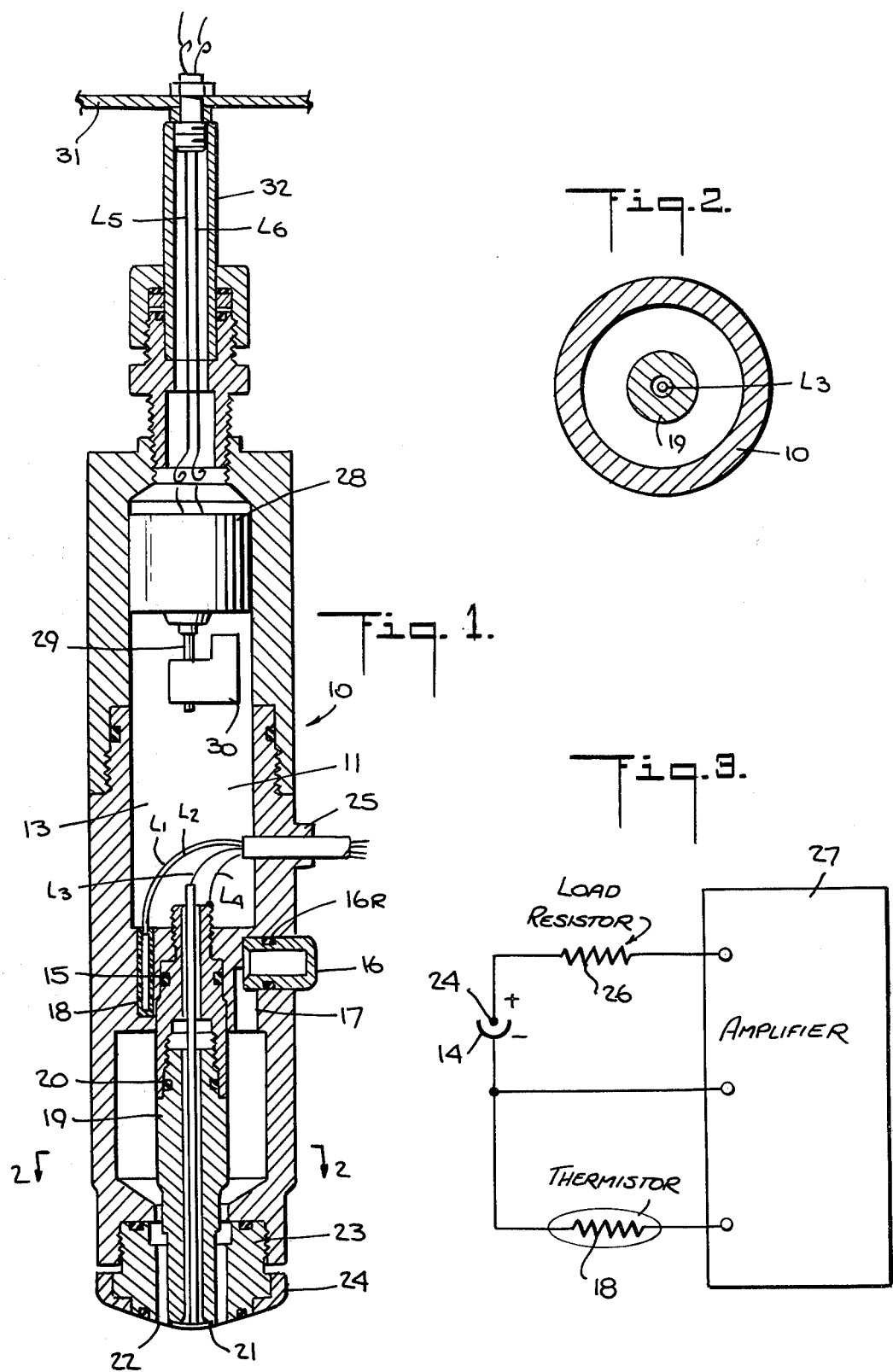

NUTATING PROBE FOR GAS ANALYSIS

BACKGROUND OF INVENTION

Field of Invention

This invention relates generally to measuring the concentration of a dissolved gas present in a stream, and more particularly to a membrane-type probe for measuring the concentration of free or total chlorine, the probe being immersible in a process tank in a water or wastewater treatment system to provide a measurement that is unaffected by the pH of the water.

Chlorination is widely used to purify water supplies. In practice, chlorine is introduced at a selected point in the water supply system, and flow then takes place into a tank or through a region of flow which is sufficient for the chlorine to act effectively on the contaminants present in the water to produce a disinfecting action. In order to determine whether the amount of chlorine present is adequate to effect disinfection, measurements are made beyond the chlorine input point. The measurement output signal may also serve to regulate the feed of chlorine into the system to insure that the amount is adequate but not excessive.

The amount of chlorine added to the water is referred to as the "dosage," and is usually expressed as parts per million (ppm). The amount of chlorine used up or consumed by bacteria, algae, organic compounds and some inorganic substances, such as iron or manganese, is designated as the "demand." Since many of the reactions with chlorine are not instantaneous, but require time to reach completion, chlorine demand is time-dependent.

The amount of chlorine remaining in the water at the time of measurement is referred to as the "residual." Residual is therefore determined by the demand subtracted from the dosage. Inasmuch as chlorine demand is time-dependent, this dependency is likewise true of chlorine residual.

When chlorine dissolves in water, a mixture of hypochlorous and hydrochloric acids is formed. Actually, the hypochlorous acid dissociates into hydrogen and hypochlorite ions. In either the hypochlorous acid or hypochlorite ion form, chlorine is called "free chlorine residual." Free chlorine residual has a highly effective killing power toward bacteria.

Should the chlorinated water contain ammonia or certain amino (nitrogen-based) compounds, as is the case with sewage, then additional compounds, called chloramines, are formed. Chloramines occur almost instantaneously, and though several reactions are possible between hypochlorous acid and ammonia, chloramines collectively are referred to as "combined chlorine residual." This combined chlorine residual has a much lower bactericidal effect than free chlorine residual. The term "total chlorine" as used herein is the sum of free and combined chlorine.

The analysis of process water or wastewater in a treatment system for chlorine in its various forms (free, combined and total) has long presented problems. The typical continuous analyzer for this purpose requires that a sample be withdrawn from the process by a pump and delivered to the analyzer, at which point various chemical reagents are added to carry out the appropriate measurement.

The presence of suspended solids in wastewater usually dictates a filter system to exclude these solids from the sample to be tested, and this in turn given rise to maintenance problems. Maintenance is also called for in connection with the supply of various chemical additives to the analyzer, this operation entailing low capacity pumps and metering hardware. These factors, taken together with the cost of the chemicals that must be supplied to the analyzer on a 24-hour per day, year round basis, result in an analyzer that is relatively difficult and expensive to install, and one that is costly to operate and maintain.

U.S. Pat. No. 3,413,199 discloses a galvanic cell usable for free chlorine analysis, while U.S. Pat. Nos. 3,948,746 and 4,176,032 disclose dissolved oxygen and chlorine dioxide probes of the membrane type. A normal requirement of membrane-type probes, such as those disclosed in the above-identified patents, is that the sample being analyzed flow past the outer surface of the membrane at a relatively high velocity to maintain analytical sensitivity. For most commercially available membrane-type probes, the required minimum flow velocity is in the order of 0.5 to 1.0 foot per second.

The reason for this rapid flow requirement is that with a sample solution that is relatively static or still, the region immediately outside the membrane becomes depleted of the species being measured by reason of the transfer of this species through the membrane to the interior of the electrochemical cell incorporated in the probe. Unless the depleted region is replenished rapidly from the bulk solution, the analytical output or sensitivity of the instrument is markedly decreased.

In those situations in which the probe is immersed in a rapidly flowing sample stream, this problem does not arise. But in most cases, except for vigorously agitated aeration tanks in sewage treatment facilities, a high velocity stream is normally not the usual environment. Thus in a typical chlorine contact tank where it is necessary to measure chlorine concentration, one encounters very slow moving, unstirred streams.

It is important not to insert a membrane-type probe into a pipeline discharging from a pump, for membrane type probes are severely affected by variations in pressure applied to membranes. While pressure-compensated probes are available, these must be fully inserted in a pipe. As a consequence, the inserted probe introduces a major obstacle in the flow path which acts to collect debris, this leading ultimately to clogging and disabling of the probe.

Another frequently used approach toward imparting the necessary velocity to the sample stream is to install a mechanical stirring device in close proxmity to the membrane of the probe. But this falls short of a satisfactory solution to the problem, for such stirrers in a contaminated stream usually collect on their stirring surfaces suspended process solids, paper, string and other foreign substances. As a result, the stirring action is inhibited. Also, the accumulated material on the stirring blades may make contact with and rupture or otherwise impair the adjacent delicate membrane of the probe.

SUMMARY OF INVENTION

In view of the foregoing, the main object of this invention is to provide an in situ membrane-type probe for measuring the concentration of a gas dissolved in the process water or wastewater of a treatment system, the probe being directly immersible into a process tank.

A significant advantage of a gas analyzing membrane-type probe in accordance with the invention is that it obviates the need to withdraw a sample from the stream, no filter being required therefor and no chemicals being added.

More specifically, an object of this invention is to provide a membrane-type probe whose membrane is permeable to the gas being analyzed, the probe being vertically mounted by a flexible coupling and being caused to nutate about its vertical axis to simulate the effect of rapid sample flow, thereby obviating the need for stirring and other external expedients to create a rapid flow in a process tank.

Also an object of this invention is to provide a membrane-type probe capable of measuring either free or total chlorine in an electrochemical cell, depending on the composition of the electrolyte, the analyzer being unaffected by variations in the pH of the sample stream.

Yet another object of the invention is to provide a chlorine analyzer which operates efficiently, accurately, and reliably for prolonged periods, and which may be manufactured at relatively low cost.

Briefly stated, these objects are attained in a probe immersible in process water or wastewater having oxygen, chlorine or another gas dissolved therein and adapted to continuously and accurately measure the concentration of the gas. The probe includes a noble metal measuring electrode, an oxidizable metal counter-electrode and an electrolyte which, in combination with the electrodes, defines an electrochemical cell whose output current depends on the amount of gas passing into the cell through a diffusion membrane permeable to the gas being analyzed. In order to simulate the effect of rapid sample flow past the membrane and thereby maintain the analytical sensitivity of the instrument, the probe is vertically supported through a flexible coupling and includes an internal motor having an unbalanced rotor secured to its shaft. Rotation of the rotor causes the probe to nutate about its vertical axis to simulate the effect of a rapid sample flow.

OUTLINE OF DRAWINGS

For a better understanding of the invention as well as other objects and further features thereof, reference is made to the following detailed description to be read in conjunction with the accompanying drawings, wherein:

FIG. 1 is a longitudinal section taken through a membrane-type probe in accordance with the invention for measuring the concentration of either free or total chlorine dissolved in a stream;

FIG. 2 is a transverse section taken in the plane indicated by line 2—2 in FIG. 1; and FIG. 3 is a schematic diagram of the probe circuit.

DESCRIPTION OF INVENTION

Chlorine Analysis

Referring now to FIGS. 1 to 2, there is shown a preferred embodiment of a membrane-type probe in accordance with the invention, the probe including a chlorine-responsive electro chemical cell disposed within the lower section of a hollow cylindrical casing 10. Casing 10 is fabricated of a suitable electrical insulating material having good structural strength, such as polyvinyl chloride or polycarbonate material.

Formed in casing 10 is an annular constriction 11 of reduced diameter which effectly divides the interior into a lower electrolyte chamber 12 and an upper motor chamber 13. Threadably received within constriction 11 and extending into electrolyte chamber 12 is a tubular anode 14 formed of silver. An O-ring 15 is provided which surrounds anode 15 at its interface with constriction 11 to prevent the leakage of electrolyte from the electrolyte chamber 12 into motor chamber 13.

A fill hole in one side of the casing is sealed by a removable stopper 16. The fill hole communicates with a duct 17 leading to electrolyte chamber 12, this chamber being filled with an electrolyte appropriate to the species to be analyzed. Since stopper 16 is submerged when the probe is immersed in the liquid being tested for dissolved chlorine, it is provided with an O-ring 16R to prevent leakage.

At a position diametrically opposed to the fill hole is a cavity within which is contained a thermistor 18 that is protectively covered with a moldable plastic such as thermally conductive epoxy. Supported coaxially within electrolyte chamber 12 is a tubular stem 19 whose upper end is socketed within the lower end of tubular anode 14 and sealed thereto by an O-ring 20. The lower end of stem 19 protrudes beyond electrolyte chamber 12, the tip of the stem having a button-shaped measuring electrode 21 mounted thereon. This measuring electrode or cathode is formed of gold.

Thus the silver anode or counter-electrode 14, the gold cathode or measuring electrode 21 and a saturated solution of an alkali bromide filling the electrolyte chamber 12 and bridging these electrodes, together define an electro chemical cell generating a current which is applied to an output resistor connected to the electrodes. The voltage developed across this resistor depends on the current flow through the cell, and, as will be explained later, this is a function of the concentration of the chlorine species being measured.

Electrolyte chamber 12 is enclosed by a semi-permeable diffusion membrane 22 which covers gold electrode 21. Membrane 22 is permeable to dissolved chlorine so that chlorine dissolved in the liquid diffuses into the electrolyte chamber. In practice, the membrane is preferably a microporous polytetrafluoroethylene material (PTFE) bonded to a polyethylene net for mechanical support. Suitable for this purpose is "Fluoropore-FG" manufactured by Millipore Corporation. This membrane has pore diameters of 0.2 micrometers ($\mu$M) and a thickness of 125 to 150 micrometers.

To stretch the membrane across the measuring electrode, its margin is clamped between an inner membrane retainer 23, threadably received within the lower end of the casing, and an outer retainer bezel 24 pressed over the inner retainer 23.

Leads $L_1$ and $L_2$ from thermistor 15 and leads $L_3$ and $L_4$ from the electrodes are taken out of the probe through a port 25, the leads being encased in a suitable waterproof cable.

When the probe is used for free chlorine analysis, the saturated solution of an alkali bromide salt (e.g., potassium bromide) is buffered to pH 4 using an acetic acid/acetate buffer, as described in greater detail in U.S. Pat. No. 3,413,199.

Free chlorine, which diffuses through membrane 22 and enters the interior of the cell, reacts with this electrolyte to produce the bromine analog of chlorine concentration. The bromine solution is electrochemically reduced at the gold measuring electrode, generating an electrical current flow in the output resistor 26 in the external circuit shown in FIG. 3. This current is proportional to bromine concentration and therefore to chlorine concentration in the process. At the same time, the silver counter-electrode 14 is oxidized, producing silver ions which are soluble in the highly concentrated bromide electrolytic solution.

In the external circuit, the electro chemical cell formed by electrodes 14 and 21 in the immersed probe are connected in series with load resistor 26 to the input of an amplifier 27, thermistor 18 being connected in a feedback voltage path. Since the thermistor is temperature-sensitive, its resistance varies as a function of the temperature of the liquid in which the probe is immersed, the feedback voltage acting to compensate for the effect of temperature on the dissolved chlorine reading. The amplifier acts to convert the current output of the cell into a useful temperature-compensated signal whose value depends solely on the dissolved chlorine concentration. In practice, the load resistor and thermistor may be housed within the casing in the motor chamber thereof.

For measuring total chlorine rather than free chlorine, one again uses as an electrolyte a saturated bromide solution, but in this instance, it is made very strongly acidic with a pH value approaching zero. I have found that not only free chlorine but also combined chlorine (chloramines) reacts with a bromide solution at pH values lower than 2.0 to produce a bromine analog of total chlorine; that is, the sum of the free and combined chlorine. The use of a bromide at pH 2.0 as the reactant for total chlorine rather than an iodide salt of a pH 4 value, as is the practice in conventional total chlorine analysis, has distinct advantages; for it avoids the precipitation of insoluble iodide salts within the probe, thereby significantly prolonging its useful life. Further, iodide solutions at acidic pH levels undergo auto-oxidation, spontaneously generating free iodine in the solution giving rise to false positive probe currents.

Nutation

A significant feature of the invention resides in a membrane-type probe assembly for gas concentration analysis which is vertically-mounted for immersion in the liquid being tested and having an internal motor to cause vibration or nutation of the entire probe assembly. This takes place at a rate and over an area of sufficient magnitude to produce the effect of rapid sample flow past the membrane, thereby avoiding depletion of the species being analyzed.

In nutation, the probe is caused to wobble with respect to the vertical axis, and it has the advantage over rotation about the vertical axis of minimizing the tendency to collect solids suspended in the process.

In the arrangement shown in FIG. 1, a miniature, preferably low-voltage, direct-current motor 28 is supported within motor chamber 11, the shaft 29 of the motor being coaxial with casing 10 so that the shaft normally lies on a vertical axis. Secured to the shaft is an eccentric or unbalanced rotor mass 30.

The probe assembly is secured to a rigid support 31 above the tank in which the probe is immersed by a flexible coupling 32 through which is extended the leads $L_5$ and $L_6$ from the motor. In practice, this coupling may take the form of a 4 or 5 inch length of $\frac{3}{4}''$ I.D. flexible polyvinylchloride tubing.

As the unbalanced mass 30 is rotated by motor 28, the entire probe assembly, which is deflectable because of its flexible coupling support, is caused to nutate with respect to its vertical axis. Thus nutation takes place at a rate which is a function of motor speed and the length of the flexible coupling. As the motor speed is increased, the effective flow rate past the membrane increases, as does the probe's analytical sensitivity, in an exponential manner approaching a maximum, essentially constant condition.

While there has been shown a nutating probe which functions to measure free or total chlorine, a similar internal motor arrangement may be used for membrane-type probes adapted to measure other gases, such as the dissolved oxygen probe disclosed in U.S. Pat. No. 3,948,746, particularly in those cases where the probe is immersed in still water as is found in clarifiers or settling tanks. Also, in order to cause vibration or oscillation of the probe assembly with respect to its normal vertical axis, instead of rotating an unbalanced mass to effect nutation, one may electromagnetically vibrate this mass.

I claim:

1. A probe immersible in a liquid having a gas dissolved therein and adapted to continuously and accurately measure the concentration of the gas, said probe comprising:
    A. a hollow casing provided with an upper motor chamber and a lower chamber having an open mouth, the casing being supported in a vertical position for immersion in the liquid by a flexible coupling attached to the upper end thereof, whereby the probe is deflectable from its normal vertical axis;
    B. a noble metal measuring electrode disposed in said electrolyte chamber adjacent said open mouth;
    C. a diffusing membrane covering said open mouth, said membrane being permeable to the gas to be measured;
    D. an oxidizable metal counter-electrode disposed in said electrolytic chamber, the chamber being filled with an electrolyte which bridges the electrodes to form a gas-sensitive electro chemical cell generating a current which is a function of the dissolved gas diffusing through said membrane; and
    E. a motor mounted in said motor chamber and having a shaft to which is attached an unbalanced rotor mass, whereby when the motor is energized, the rotating mass causes the probe to nutate relative to its normal vertical axis to simulate the effect of a rapid flow of the liquid relative to the membrane.

2. A probe as set forth in claim 1, wherein said coupling is a flexible tube through which is extended the power leads for said motor.

3. A probe as set forth in claim 1, wherein said gas is chlorine and said diffusing membrane is formed of PTFE material.

4. A probe as set forth in claim 3, wherein said measuring electrode is gold.

5. A probe as set forth in claim 4, wherein said counter-electrode is silver.

6. A probe as set forth in claim 5, wherein said electrolyte is a saturated solution of an alkali bromide salt.

7. A probe as set forth in claim 6 for measuring free chlorine wherein said solution is buffered to about pH 4.

8. A probe as set forth in claim 7, wherein the buffer is acetic acid/acetate.

9. A probe as set forth in claim 6 for measuring total chlorine, wherein said solution has a pH no greater than 2.

* * * * *